US00PP36733P2

(12) United States Plant Patent
Helvick

(10) Patent No.: US PP36,733 P2
(45) Date of Patent: Jun. 10, 2025

(54) ***LANTANA* PLANT NAMED 'RHLC2019'**

(50) Latin Name: *Lantana camara*
Varietal Denomination: RHLC2019

(71) Applicant: Rhonda Helvick, Madison, GA (US)

(72) Inventor: Rhonda Helvick, Madison, GA (US)

( * ) Notice: Subject to any disclaimer, the term of this patent is extended or adjusted under 35 U.S.C. 154(b) by 0 days.

(21) Appl. No.: 18/809,633

(22) Filed: Aug. 20, 2024

(51) Int. Cl.
*A01H 5/02* (2018.01)
*A01H 6/86* (2018.01)

(52) U.S. Cl.
USPC ..... Plt./227

(58) Field of Classification Search
USPC ..... Plt./227
See application file for complete search history.

*Primary Examiner* — Susan McCormick Ewoldt
(74) *Attorney, Agent, or Firm* — Cassandra Bright

(57) ABSTRACT

A new and distinct cultivar of *Lantana* plant named 'RHLC2019', characterized by its low growing, layered and spreading and mounding growth habit; leathery, scabrous, lustrous dark green foliage; continuous flowering; and red flower buds that open to orange-yellow and age to vivid red. There are no other cultivars of *Lantana* with this combination of characteristics known to the inventor.

3 Drawing Sheets

Genus and species of plant claimed: *Lantana camara.*
Variety denomination: 'RHLC2019'.

BACKGROUND OF THE INVENTION

The present invention relates to a new and distinct cultivar of *Lantana* plant, botanically known as *Lantana camara*, and hereinafter referred to by the cultivar name 'RHLC2019'.

The new *Lantana* plant originated from a controlled cross between *Lantana camara* 'UF-1013A-2A' (U.S. Plant Pat. No. 29,292) female parent, and *Lantana camara* 'Chapel Hill Gold' (U.S. Plant Pat. No. 21,539), male parent, as part of a planned breeding program to develop low growing, continuously flowering *Lantanas* with dark green foliage and cold hardiness to USDA Hardiness Zone 7. The cultivar 'RHLC2019' originated and was discovered in a cultivated environment in Madison, Georgia.

Asexual reproduction of the new cultivar by stem cuttings in Madison, GA has shown that all the unique features of this new *Lantana*, as herein described, are stable and reproduced true-to-type through successive generations of such asexual propagation.

SUMMARY OF THE INVENTION

Plants of the new cultivar 'RHLC2019' have not been observed under all possible environmental conditions. The phenotype may vary somewhat with changes in light, temperature, soil and rainfall without, however, any variance in genotype.

The following traits have been repeatedly observed and are determined to be unique characteristics of 'RHLC2019'. These characteristics in combination distinguish 'RHLC2019' as a new and distinct cultivar:

1. Low growing, mounding and spreading growth habit.
2. Leathery, scabrous, lustrous dark green, fragrant foliage.
3. Continuous flowering.
4. Red flower buds that open to orange-yellow and age to a vivid red.

5. Cold hardy to US Hardiness zone 7.

There are no other cultivars of *Lantana* with this combination of characteristics known to the inventor.

PARENTAL COMPARISON

Plants of the new *Lantana* camara 'RHLC2019' differ from plants of the female parent, 'UF-1013A-2A', (U.S. Plant Pat. No. 29,292) primarily in flower hardiness. 'UF-1013A-2A' is hardy to zone 9, whereas 'RHLC2019' is hardy to zone 7. The flower of 'UF-1013A-2A' opens yellow and ages to a red orange, but 'RHLC2019' opens a strong orange yellow and ages to a vivid red.

Plants of the new *Lantana* 'RHLC2019' can be compared to plants of *Lantana camara* 'Chapel Hill Gold' (U.S. Plant Pat. No. 21,539), the male parent, mainly in flower color. 'Chapel Hill Gold' flowers start off bright yellow gold and remain that color. 'Chapel Hill Gold' habit is spreading, whereas 'RHLC2019' has a mounding and spreading habit. Both plants are similar due to their cold hardiness in USDA zone 7.

COMMERCIAL COMPARISON

Plants of the new *Lantana* 'RHLC2019' can be compared to *Lantana camara* 'Dallas Red' (unpatented) mainly in flower color and cold hardiness. 'Dallas Red' flowers start off red, turn to orange, and yellow with aging. 'RHLC2019' flowers start off a strong orange yellow fading to a vivid red. 'Dallas Red' is hardy to zone 8, but 'RHLC2019' is hardy to zone 9.

BRIEF DESCRIPTION OF THE DRAWINGS

The accompanying color photographs illustrate the flower and foliage characteristics and the overall appearance of the new *Lantana*, showing the colors as true as it is reasonably possible to obtain in color reproductions of this type. Colors in the photographs may differ slightly from the color values cited in the detailed botanical description which accurately describe the colors of the new *Lantana*.

DETAILED DESCRIPTION

Figure 1:
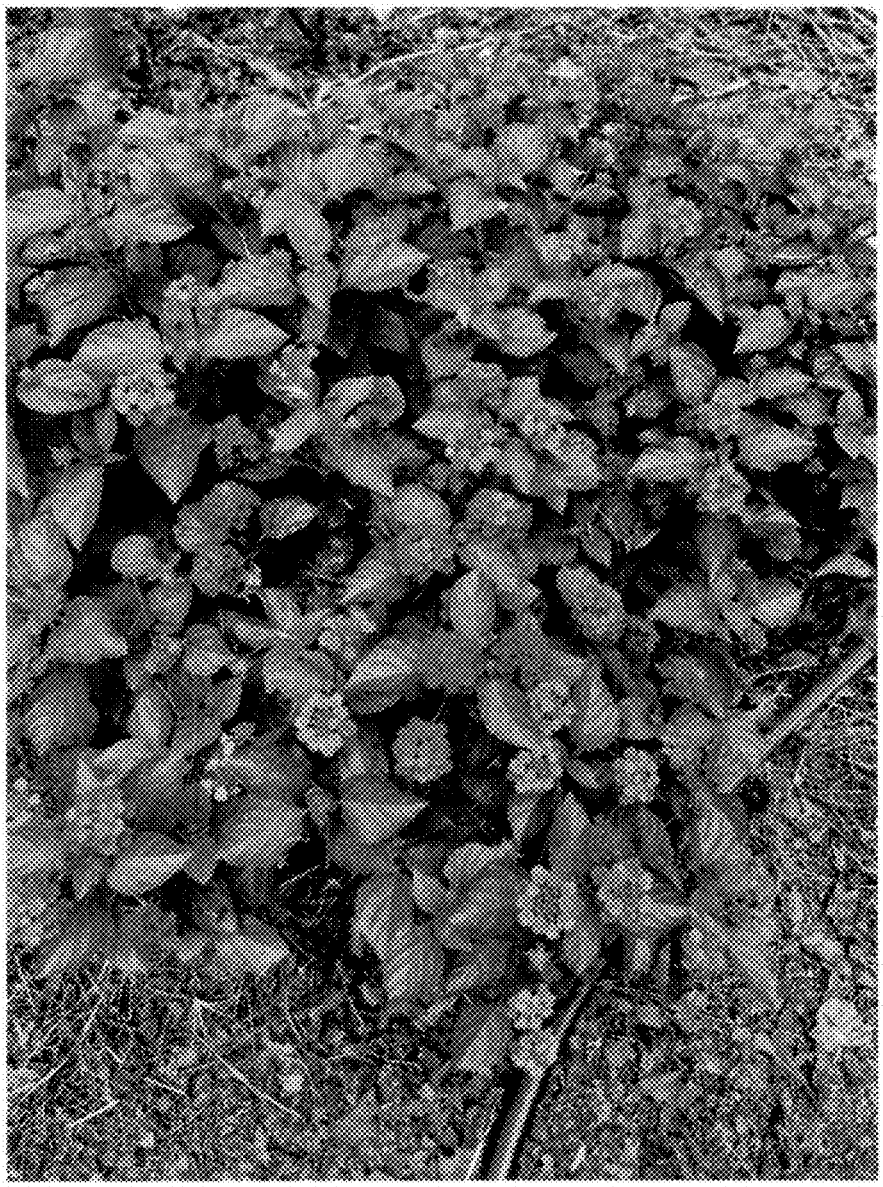
FIG. 1 illustrates the overall appearance of a 4-year-old 'RHLC2019' in the ground.
Figure 2:
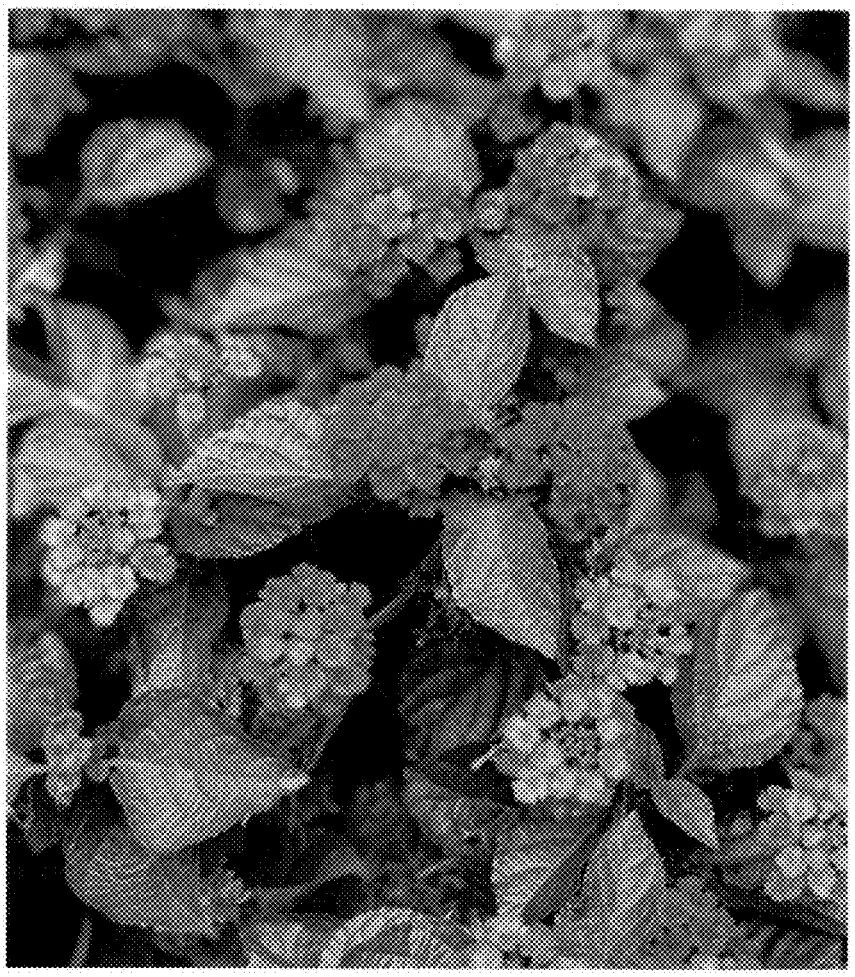
FIG. 2 illustrates a close-up view of the inflorescences in a 4-year-old plant in the ground.
Figure 3:
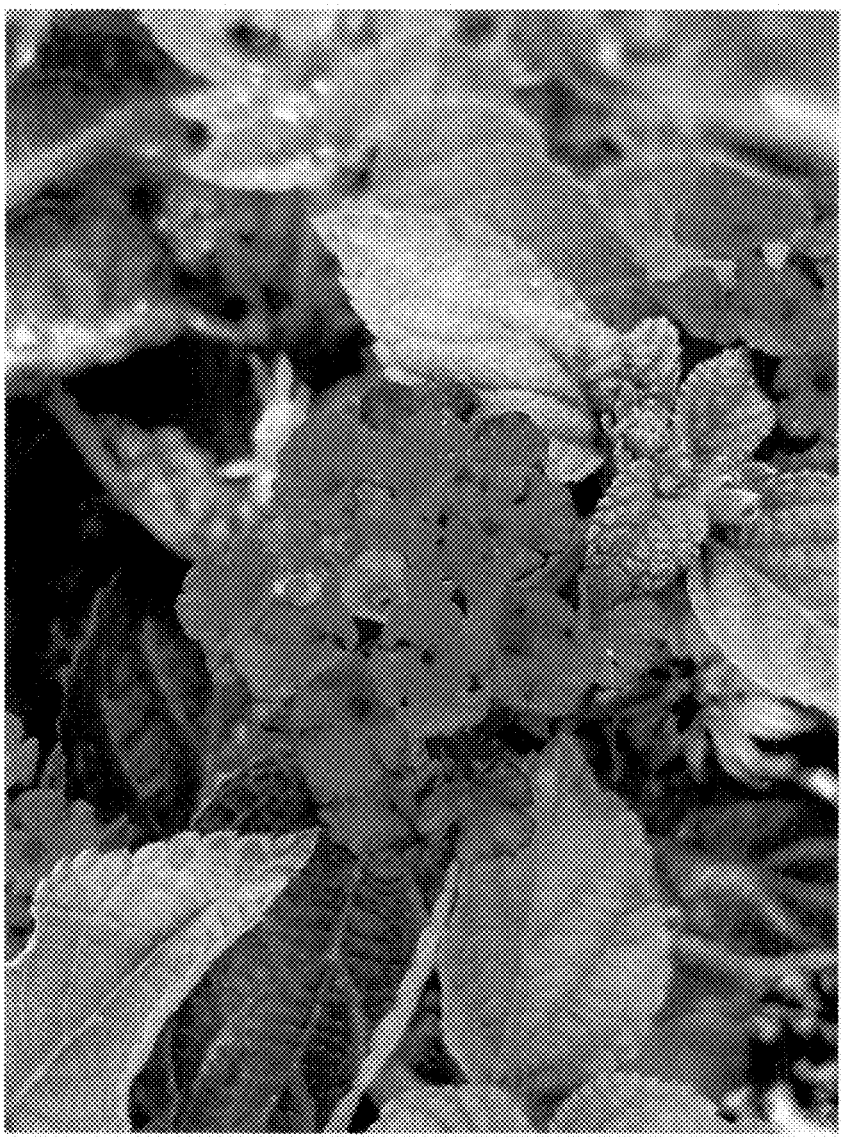
FIG. 3 illustrates a close-up of the flower in a 6-month-old plant grown in a container.

In the following description, color references are made to The Royal Horticultural Society Colour Chart, 2015 Edition, except where general terms of ordinary dictionary significance are used. Plants used for the description were approximately five-years-old and were grown the full sun under outdoor conditions in a nursery in Madison, GA.

Botanical classification: *Lantana camara* 'RHLC2019'. Parentage: Female or seed parent: *Lantana camara* 'UF-1013A-2A' (U.S. Plant Pat. No. 29,292). Male or pollen parent: *Lantana camara* 'Chapel Hill Gold' (U.S. Plant Pat. No. 21,539) (controlled-pollination). Propagation: stem cuttings. Time to initiate roots, summer: about 10 days at 32° C. Time to produce a rooted young plant, summer about 4 months at 32° C.

PLANT DESCRIPTION

Herbaceous flowering plant, subshrub, low growing, mounding and spreading growth habit. Freely branching habit with about six to eight primary lateral branches per plant; each primary lateral branch with potentially two secondary lateral branches developing at each node. Pinching enhances lateral branch development. Length about 30 cm with a diameter of 3 mm.

Root description: numerous, fine, fibrous and well-branched. Color: NN155A.

Plant size: about 66 cm in height from the media level to the top of the inflorescences, and about 38 cm in diameter.

Plant Vigor: Medium. Plants grow approximately 2 feet during the growing season.

Stems: Young stems have a diameter of about 3 mm and a squarish shape. Mature stems have a diameter of about 4 mm or more and a rounded shape. Quantity of main branches per plant 6-8. Length of stems about 30 cm.

Stem strength: strong, but flexible.

Stem texture: coarse, pubescent.

Stem color (young): 144A. Color (mature): 199C.

Internode length: about 3 cm.

VEGETATIVE BUDS

Opposite in arrangement, valvate, ovoid, pubescent. Color: Yellow-Green 144A. Size: about 1 mm in length and about 1 mm in width.

FOLIAGE DESCRIPTION

Arrangement: opposite, simple. Length: about 4.5 cm. Width: about 3.5 cm. Shape: ovate. Apex: acute. Base: cuneate. Margin: dentate.

Texture (upper surface): leathery, moderately waxy, with scabrous pubescence. Texture (lower surface): rough, with hispid pubescence.

Venation pattern: pinnate. Venation color (upper surface): 144B. Venation color (lower surface): 144B.

Fragrance: pungent, mint-like.

Color of developing foliage (upper surface): 146A. Color of developing foliage (lower surface): 146B. Color of mature foliage (upper surface): 146A. Color of mature (lower surface): 146B.

Petiole length: about 5 mm. Petiole diameter: about 2 mm. Petiole texture, both surfaces: hispid pubescence. Petiole color (upper and lower surfaces): 144A.

Quantity of Leaves: There are about 25 leaves per branch.

Leaf Aspect: The leaf apex is at a 45° angle from the branch.

FLOWER DESCRIPTION

Flower type and habit: small salverform flowers arranged in axillary corymbs; flowers face mostly upward or outward. Flowers are self-cleaning. Freely flowering with potentially two inflorescences per node; typically, about 22 to 28 flowers per corymb. Quantity of inflorescence per plant about 18. Natural flowering season: spring until the first frost in fall; flowering is continuous. Flower longevity on the plant: about one week. Fragrance: none observed. Inflorescence diameter: about 3 cm. Inflorescence height: about 2.5 cm.

Flower bud length: about 1 cm. Flower bud diameter: about 3 mm. Flower bud shape: oblong. Flower bud color: Red 45A. Flower bud shape is cubic (squared) with softened, rounded edges.

Flower Appearance: Flared trumpet, corolla fused, four-parted; flowers roughly rectangular in shape. Diameter: about 1 cm. Corolla tube length: about 1 cm. Depth (height): about 1.5 cm. Throat diameter: about 1.5 mm. Tube length: about 1.1 cm.

Pedicels: none observed, flowers not stalked, sessile.

Arrangement: Single whorl of four petals, fused into flared trumpet. Diameter: about 9 mm by 10 mm. Depth (height): about 1.5 cm. Throat diameter: about 1 mm. Tube length about 1 cm.

PETALS

Petal length from throat: about 5 mm for the upper petal, about 4 mm for the lower petal, and about 4 mm for the lateral petals.

Petal width: about 6 mm for the upper petal, about 5 mm for the lower petal, and about 4 mm for the lateral petals.

Petal shape: Spatulate to somewhat orbicular. Petal apex: obtuse. Petal base: fused. Petal margin: entire. Petal texture, upper and lower surfaces: smooth, glabrous.

Petal color (young): upper surface: 17A and lower surface: 18A. Color of throat: 17A. Color of corolla tube: 17A.

Petal color (mature): upper and lower surfaces, throat, and corolla tube: 45B. Petal color (aged): upper and lower surfaces, throat, and corolla tube: 42A.

SEPALS

Arrangement/appearance: one sepal per flower at the base of the corolla, leaf-like. Length is about 5 mm. Width is about 2 mm. Shape: lanceolate. Apex: acute. Margin: entire. Texture, upper and lower surface: scabrous.

Sepal color, upper and lower surfaces: 144A.

PEDUNCLES

Length: about 1.5 cm. Diameter: about 1 mm. Angle: about 45 degrees from the stem. Texture: pubescent. Strength: flexible, but strong. Color: 144A.

ANDROECIUM

Quantity/arrangement: four per flower, adnate to the inside of the corolla tube. Anther shape: oblong. Anther length: 1 mm. Anther width: less than 1 mm. Anther color: 15A. Filament length: 1 mm. Filament color: 155D. Pollen amount: produced in very small quantities, and 13B in color.

GYNOECIUM

Quantity: one inferior pistil per flower. Pistil length: about 3.5 mm. Pistil color: 145C. Stigma shape: rounded. Stigma size: about 1 mm in diameter. Stigma length: less than 1 mm. Stigma color: 145C. Style length: about 1.5 mm. Style color: 145C. Ovary size: about 1 mm in diameter. Ovary color: 145A.

FRUIT

Type/appearance: drupe. Shape: round. Diameter: about 5 mm. Texture: smooth. Mature color: 202A. Number per infructescence: ranges from zero to about five.

SEED

Amount produced: one seed per fruit. Size: diameter about 2.5 mm. Texture: smooth. Color: 199D.

DISEASE/PEST RESISTANCE

Plants of the claimed *Lantana* cultivar grown in the garden have not been noted to be susceptible or resistant to pathogens and pests common to *Lantana*.

What is claimed is:

1. A new and distinct *Lantana* plant named 'RHLC2019', as illustrated and described herein.

* * * * *